United States Patent
Groszmann et al.

(10) Patent No.: US 11,660,391 B2
(45) Date of Patent: May 30, 2023

(54) DRUG DELIVERY SYSTEMS AND METHODS WITH BACK PRESSURE SENSING

(71) Applicant: AMGEN INC., Thousand Oaks, CA (US)

(72) Inventors: Daniel Eduardo Groszmann, Belmont, MA (US); Scott Robert Gibson, Granada Hills, CA (US)

(73) Assignee: AMGEN INC., Thousand Oaks, CA (US)

( * ) Notice: Subject to any disclaimer, the term of this patent is extended or adjusted under 35 U.S.C. 154(b) by 209 days.

(21) Appl. No.: 16/745,693

(22) Filed: Jan. 17, 2020

(65) Prior Publication Data

US 2020/0238006 A1 Jul. 30, 2020

Related U.S. Application Data

(60) Provisional application No. 62/796,381, filed on Jan. 24, 2019.

(51) Int. Cl.
*A61M 5/168* (2006.01)
*A61M 5/142* (2006.01)
(Continued)

(52) U.S. Cl.
CPC .... *A61M 5/16836* (2013.01); *A61M 5/14212* (2013.01); *A61M 5/2033* (2013.01);
(Continued)

(58) Field of Classification Search
CPC .......... A61M 5/16836; A61M 5/14212; A61M 5/2033; A61M 5/2459; A61M 5/3157;
(Continued)

(56) References Cited

U.S. PATENT DOCUMENTS

| | | |
|---|---|---|
| 2003/0216683 A1 | 11/2003 | Shekalim |
| 2008/0097287 A1 | 4/2008 | Nelson et al. |
| 2015/0190588 A1* | 7/2015 | Hanson ........... A61M 5/36 604/123 |
| 2018/0236185 A1* | 8/2018 | Säll ............ A61M 5/2033 |
| 2018/0318501 A1* | 11/2018 | Hochman ........ A61M 5/46 |

FOREIGN PATENT DOCUMENTS

WO WO-2017007952 A1 * 1/2017 ........ A61M 5/14248

OTHER PUBLICATIONS

Meritmedical, Meritrans, 2015, p. 2, https://cloud.merit.com/catalog/Brochures/400545002-B.pdf (Year: 2015).*
(Continued)

*Primary Examiner* — Theodore J Stigell
*Assistant Examiner* — Rachel T. Smith
(74) *Attorney, Agent, or Firm* — Marshall, Gerstein & Borun LLP

(57) ABSTRACT

Systems and methods for injecting a drug and detecting tissue induced back pressure are disclosed. A drug delivery system may include a reservoir filled or fillable with a drug, an administration member connected or connectable in fluid communication with the reservoir, a drive assembly, and a pressure sensor. The administration member may be configured for insertion into and subsequently retraction from a patient. The drive assembly may be configured to urge the drug from the reservoir to deliver a dose of the drug to the patient via the administration member. The pressure sensor may be configured to detect tissue back pressure during use of the drug delivery system, including after dose completion and prior to retraction of the administration member. The drug delivery system may be controlled in a manner that accounts for the tissue back pressure measurement.

21 Claims, 4 Drawing Sheets

(51) Int. Cl.
*A61M 5/20* (2006.01)
*A61M 5/24* (2006.01)
*A61M 5/315* (2006.01)

(52) U.S. Cl.
CPC ........ *A61M 5/2459* (2013.01); *A61M 5/3157* (2013.01); *A61M 2205/18* (2013.01); *A61M 2205/3344* (2013.01)

(58) Field of Classification Search
CPC ...... A61M 2205/18; A61M 2205/3344; A61M 2005/14256; A61M 2005/1726; A61M 5/145; A61M 5/1684; A61M 5/16804; A61M 2005/14208; A61M 5/16854; A61M 2205/3331; A61M 2005/1588; A61M 5/1723
See application file for complete search history.

(56) References Cited

OTHER PUBLICATIONS

Wayback Machine for "Meritrans", https://web.archive.org/web/2015*/https://cloud.merit.com/catalog/Brochures/400545002-B.pdf (Year: 2022).*
Sensor Products, Tactilus, 2011, https://www.sensorprod.com/glossary/tactile-pressure-sensor/tactile-pressure-sensor.php (Year: 2011).*
Wayback Machine for "Tactilus", https://web.archive.org/web/20110601000000*/https://www.sensorprod.com/glossary/tactile-pressure-sensor/tactile-pressure-sensor.php (Year: 2022).*
International Application No. PCT/US2020/013886, International Search Report and Written Opinion, dated May 14, 2020.

* cited by examiner

DRUG DELIVERY SYSTEMS AND METHODS WITH BACK PRESSURE SENSING

CROSS-REFERENCE TO RELATED APPLICATION

Priority is claimed to U.S. Provisional Patent Application No. 62/796,381, filed Jan. 24, 2019, the entire contents of which are incorporated herein by reference.

FIELD OF DISCLOSURE

The present disclosure generally relates to drug delivery systems and, more particularly, drug delivery systems facilitating the injection of a drug in liquid form.

BACKGROUND

Parenteral delivery of various drugs, i.e., delivery by means other than through the digestive track, has become a desired form of drug delivery. Bypassing the stomach can prevent catalytic enzymes from degrading active ingredients in the drug and increases the likelihood that a necessary amount of a drug, at a desired concentration, reaches a targeted site. Furthermore, growth in treatments involving biologics, which oftentimes are injected in liquid form, has made parenteral delivery more common.

A typical injection involves the use of a drug delivery device having a reservoir and an administration member such as a hollow cannula or needle. A pointed end of the administration member is inserted into the patient and the reservoir is actuated to deliver the drug to the patient via the administration member. Considerable attention has been devoted to ensuring that such drug delivery devices are configured to deliver a prescribed volume or dose of a drug to the patient. This is because many treatments require the delivery of an exact amount of a drug, with even small variations being unacceptable. Under delivery can, for example, compromise the efficacy of the drug, while over delivery can increase the risk of adverse side effects, for example.

Self-injection with a drug delivery device introduces additional risk of suboptimal delivery. Patients who are not experienced with self-injecting or in a weakened state due to an illness, for example, are prone to operating the drug delivery device improperly. Further, even if the drug delivery device is operated according to its intended use, environmental and/or operating conditions including the patient's physiology can result in incomplete delivery.

As described in more detail below, the present disclosure sets forth drug delivery systems and related methods embodying advantageous alternatives to existing systems and methods, and that may address one or more of the challenges or needs mentioned herein, as well as provide other benefits and advantages.

SUMMARY

One aspect of the present disclosure provides a drug delivery system. The drug delivery system may include a reservoir filled or fillable with a drug, an administration member connected or connectable in fluid communication with the reservoir, a drive assembly, and a pressure sensor. The administration member may be configured for insertion into and retraction from a patient. The drive assembly may be configured to actuate the reservoir to deliver the drug to the patient via the administration member. The pressure sensor may be configured to detect tissue back pressure during use of the drug delivery system.

Another aspect of the present disclosure provides a method of operating a drug delivery system. The method includes: (a) automatically injecting an end of an administration member initially stored within an interior space of a housing of the drug delivery system into a patient; (b) automatically actuating a reservoir to deliver a dose of the drug to the patient via the administration member; and (c) using a pressure sensor included in the drug delivery system to monitor tissue back pressure after finishing actuating the reservoir to deliver the dose of the drug to the patient.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings is necessarily to scale.

DETAILED DESCRIPTION

Figure 1:
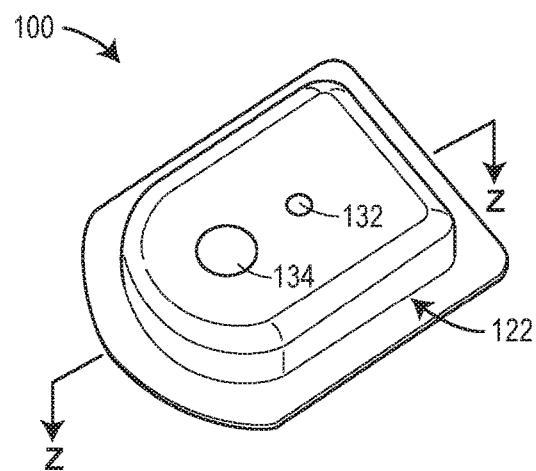
FIG. 1 is an exterior perspective view of a drug delivery system according to one embodiment of the present disclosure.

A drug, also referred to herein as a medicament or drug product, may be injected or infused using a variety of different approaches, technologies, and systems. For example, a drug may be filled into a reservoir (or container) in the form of a syringe, and then the syringe may be used to manually inject the drug via a needle inserted into the patient. Alternatively, the drug may be filled into a reservoir in the form of a syringe or other appropriate primary container, e.g., a cartridge, and then the pre-filled syringe or other container may be combined with an autoinjector configured to automate movement of a plunger within a bore of the syringe or container, and optionally insertion of a needle into the patient. For example, the autoinjector may include a drive assembly (e.g., a motor, spring(s), propellant reservoir, etc.) that causes the container to move within a housing and/or the plunger to move within the bore of the container upon manipulation of an activation element (e.g., by depressing a button or retracting a needle guard). As a still further alternative, the drug may be filled into a reservoir, and the reservoir (prior to or after filling) may be combined with a wearable device have a mechanism for automatically inserting a needle and/or cannula into the patient and a drive assembly (which may take the form of, e.g., a motor, spring(s), propellant reservoir, etc.) for automatically actuating the reservoir. The wearable device may include a housing that is releasably attachable to a patient's skin to form an on-body drug delivery system, for example.

In whatever form the drug delivery system may take, an administration member such as a needle or cannula is inserted into the patient and a force is applied to expel the drug from the reservoir through the administration member into the patient's tissue (e.g., subcutaneous tissue, muscular tissue, etc.). The force applied must overcome both internal resistance within the drug delivery system and resistance from the patient's tissue as the tissue makes space for the injected volume of the drug. The resistance from the patient's tissue results in tissue back pressure. Tissue back pressure is present both during an injection and for a period of time following the injection. Tissue back pressure gradually decays over time as the tissue absorbs or accommodates the drug. Immediately following the injection, however, tissue back pressure can be significant. As a consequence, tissue back pressure can cause the drug to leak out of the skin at the injection site. This results in what is referred to as a "wet" injection, which is not desirable for patient experience. Furthermore, and more significantly, leakage (also referred to as back-flow or reflux) results in a smaller than intended dose of the drug being delivered to the patient. Drug efficacy can be compromised as a result.

One way to inhibit or prevent a wet injection is to leave the administration member in place at the injection site until the tissue back pressure falls below a certain threshold. In some cases, this threshold (identified in FIG. 7 as $P_b$) may be equal to approximately (e.g., ±10%) 0.5 pounds per square inch (psi). By leaving the administration member in place, it can act as a plug that prevents or inhibits the drug from leaking out through the hole formed in the skin by inserting the administration member. The time required for the tissue back pressure to fall below $P_b$ may vary depending on, for example, delivery conditions and the patient's physiology. Accordingly, setting a fixed waiting period for the patient or drug delivery system to remove the administration member may not be a reliable way to prevent leakage.

Tissue back pressure tends to increase with higher injection rates. It is thought that this is caused by the tissue network experiencing higher mechanical strain in the case of high injection rates and consequently pushing back on the drug with more force. Certain drugs such as injectable biologics are seeing a trend towards higher volume delivery. This, in part, is due to a trend towards less frequent dosing, which requires the delivery of a larger dose at any given injection. Larger doses, in turn, have been met with higher injection rates, in order to limit injection time. Accordingly, the trend towards higher volume delivery and the attendant higher injection rates has increased the likelihood of wet injections. Furthermore, certain drugs including injectable biologics are being produced in more viscous formulations than in the past. Higher drug viscosities tend to increase tissue back pressure and therefore increase the possibility of a wet injection.

This disclosure focuses on drug delivery systems that are capable of sensing tissue back pressure both during and after an injection event. In doing so, a drug delivery system according to the present disclosure may alter its operation and/or instruct a patient to operate the drug delivery system in a manner that reduces the possibility of drug leakage at the injection site post-injection. The present disclosure also provides sensor configurations and arrangements that facilitate tissue back pressure and other pressure measurements, including drive pressure measurements, within a drug delivery system. According to certain embodiments, a single sensor may be configured to detect drive pressure during operation of a drive assembly to expel a dose of a drug from a reservoir for delivery into a patient, and additionally, tissue back pressure after drug delivery is complete. Alternative embodiments may utilize separate sensors for making the drive pressure and tissue back pressure measurements.

Figure 2:
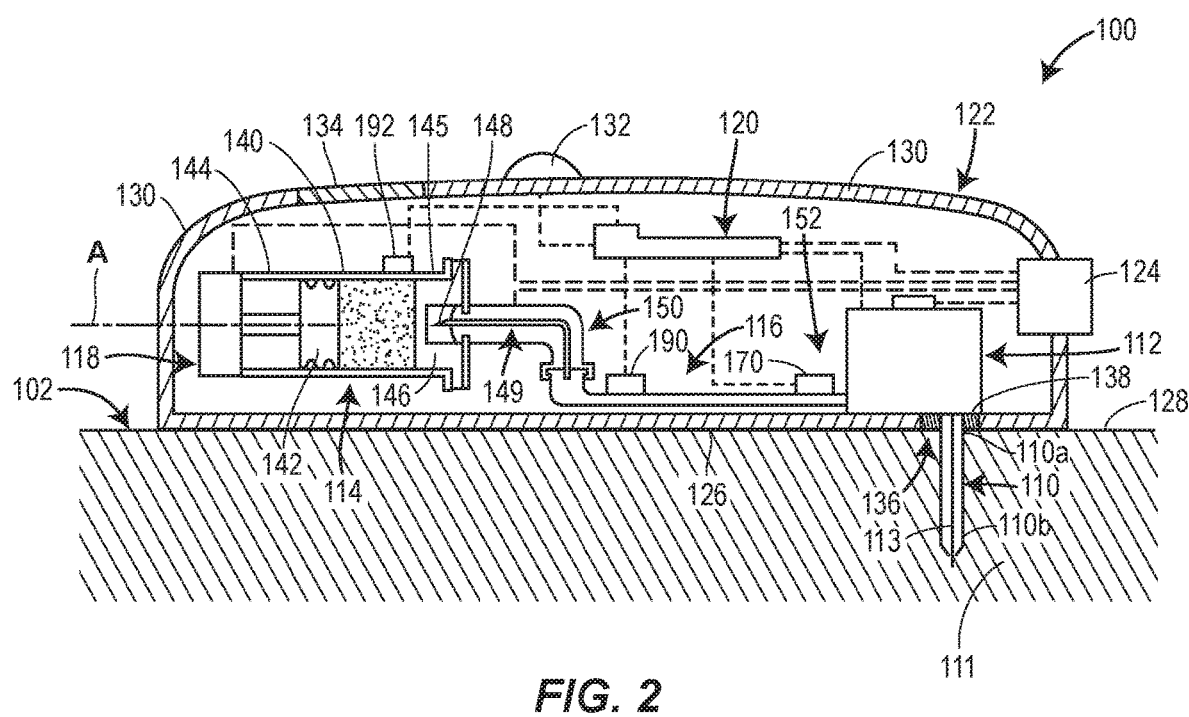
FIG. 2 is a schematic cross-sectional view of the drug delivery system depicted in FIG. 1 taken along line Z-Z.

FIGS. 1 and 2 illustrate a drug delivery system 100 for injecting a drug into tissue (e.g., subcutaneous tissue, muscular tissue, etc.) of a patient 102. The drug may be, but is not limited to, various biologic drugs including peptides, peptibodies, and antibodies. The drug may be in a fluid or liquid form, and in certain formulations, may have a high viscosity. In some versions, the drug delivery system 100 may be configured to automatically deliver a fixed or a patient/operator-settable dose of the drug in the form of a bolus over a controlled or selected period of time. Furthermore, the drug delivery system 100 may be intended for self-administration by the patient, or may be operated by a formally-trained healthcare professional to administer the injection.

Various implementations and configurations of the drug delivery system 100 are possible. The drug delivery system 100 may be configured as a single-use, disposable injector, or alternatively, as a multiple-use reusable injector. In the embodiment illustrated in FIGS. 1 and 2, the drug delivery system 100 is configured as an on-body injector that is releasably attached to a patient's skin over the duration of an injection. In alternative embodiments, the drug delivery system can be configured as an autoinjector or pen-type injector that is held in the hand of a patient or user over the duration of the injection. In still further alternative embodiments, the drug delivery system can be a syringe that is manually operable to perform an injection, as opposed to on-body injector and autoinjector versions where the drug delivery system may be able to automatically insert the administration member, automatically expel the drug from the reservoir, and/or automatically retract the administration member following the injection, and/or have other automated features or functions.

Referring to FIG. 2, the drug delivery system 100 includes, in some embodiments, an administration member 110, an insertion/retraction mechanism 112, a reservoir 114, a fluid pathway connection assembly 116, a drive assembly 118, and a controller 120, each of which may be disposed within an interior space of a main housing 122. Collectively the administration member 110, insertion/retraction mechanism 112, fluid pathway connection assembly 116, drive assembly 118, main housing 122, and/or other elements may be referred to herein as a drug delivery device, and that device may be combined with the reservoir 114, controller 120, and/or other elements to form the drug delivery system 100.

The administration member 110 may be hollow and have a first end 110a connected or connectable in fluid communication with the reservoir 114 via the fluid pathway connection assembly 116, and a second end 110b to be inserted into the patient's tissue 111. In some embodiments, the administration member 110 may take the form of a cannula made of a relatively flexible material and have a relatively blunt tip at the second end 110b; whereas, in other embodiments, the administration member 110 may take the form of a needle made of a relatively rigid material and have a sharpened point at the second end 110b. The administration member 110 may be integrated with other elements of the drug delivery system 100, or the administration member 110 may be separate from the other elements of the drug delivery system 100 until immediately prior to use.

According to certain embodiments, including the one illustrated in FIG. 2, the drug delivery system 100 may further include a trocar or introducer member 113 to introduce the second end 110b of the administration member 110 into the patient's tissue 111, although this is not required according to each embodiment of the disclosure. The introducer member 133 may, in certain embodiments, be withdrawn back into the housing 122 of the drug delivery system 100, thereby leaving the second end 110b of the administration member 110 inside the patient for a subcutaneous, intramuscular, etc. injection of the drug. In such embodiments, the administration member 110 may be a cannula (e.g., a blunt cannula) constructed of a relatively flexible or soft material such as plastic or another polymer, whereas the introducer member 113, which may be a solid or hollow needle or trocar, may be constructed a relatively rigid or hard material such as metal. Accordingly, the administration member 110 may be constructed of a more flexible material than introducer member 113. The relative flexibility of the administration member 110 may allow it to be disposed within the patient's tissue 111 for a period of a time (e.g., minutes, hours, days, etc.) without causing pain or significant discomfort to the patient. In other embodiments (not illustrated), the introducer member 113 may be omitted, and instead the insertion/retraction mechanism 112 may insert only the administration member 110 into the patient.

In certain embodiments, although the introducer member 113 may be retracted from the patient's tissue 111 prior drug delivery, the drug may pass through the introducer member 113 prior to being injected into the patient tissue 111. In such embodiments, the introducer member 113 may have a hollow interior passage which remains in fluid communication with and upstream of the administration member 110 after retraction of the introducer member 113. Accordingly, the drug may flow through the introducer member 113, then into the administration member 110, and finally into the patient's tissue 111. In this way, the introducer member 113 may be said to correspond to an administration member as it is at least momentarily inserted into the patient and is connected in fluid communication with the reservoir 114 during drug delivery, even though the drug may not exit the introducer member 113 directly into the patient.

Still referring to FIG. 2, an activation member 124 (e.g., a user-depressible button, touchscreen, microphone, etc.) may protrude through or otherwise be disposed at an exterior surface of the housing 122 and may be configured to initiate operation of drug delivery system 100 by activating, via mechanical and/or electrical means (shown in dotted lines in FIG. 2), the insertion/retraction mechanism 112, the fluid pathway connection assembly 116, the drive assembly 118, the controller 120, and/or other mechanisms and/or electronics. In embodiments where the activation member 124 is a button that is depressed or otherwise physically moved by a user or patient, the activation member 124 may be configured to exert the motive force needed to activate the insertion/retraction mechanism 112, the fluid pathway connection assembly 116, the drive assembly 118, the controller 120, and/or other elements. In such embodiments, the activation member 124 may be physically connected to, either directly or indirectly via a mechanical linkage, the insertion/retraction mechanism 112, the fluid pathway connection assembly 116, the drive assembly 118, and/or other mechanisms such that manually depressing or otherwise interacting with the activation member 124 supplies the motive force necessary to activate these elements.

For example, in some embodiments, manually depressing the activation member 124 may cause the fluid pathway connection assembly 116 to move towards a stationarily-positioned reservoir 114, or alternatively, cause a movable reservoir 114 to move towards the stationarily-positioned fluid pathway connection assembly 116, and thereby cause a container access needle to penetrate through a seal member (e.g., a pierceable septum) into a drug-containing chamber of the reservoir 114. Additionally or alternatively, the activation member 124 may operate as an input device that transmits an electrical and/or mechanical signal to the controller 120, which in turn may execute programmable instructions to control operation of the insertion/retraction mechanism 112, the drive assembly 118, the fluid pathway connection assembly 116, and/or other elements. In such embodiments, the controller 120 may include a processor (e.g., a microprocessor) and a non-transitory memory for storing the programmable instructions to be executed by the processor. Furthermore, in such embodiments, the drive assembly 118 may include an internal actuator (e.g., an electric motor, a pneumatic or hydraulic pump, and/or a source of pressurized gas or liquid in the form of a propellant reservoir) which is separate from the activation member 124 and which, in response to an electrical control signal received from the controller 120, exert the motive force needed to activate the insertion/retraction mechanism 112, the fluid pathway connection assembly 116, and/or other elements.

With continued reference to FIG. 2, the housing 122 may include a bottom wall 126 configured to be releasably attached (e.g., adhered with an adhesive) to skin surface 128 of the patient 102, and a top wall 130 including an output device 132 and a window 134 for viewing the reservoir 114. The output device 132 is controllable to notify and/or provide information to the patient or user about the operational state or condition of the drug delivery system 100. The output device 132 may be any device suitable for conveying information to the patient or user including a display (e.g., a liquid crystal display), a touchscreen, a light (e.g., a light emitting diode), a vibrator (e.g., an electro-mechanical vibrating element), a mechanical or color-changing flag member, a speaker, an alarm, and/or any other suitable device, or any combination thereof. As described below in more detail, the output device 132 may be controlled (e.g., activated or de-activated) to alert or inform the patient or user after dose completion that the tissue back pressure remains above a certain threshold and thus the patient or user should wait to remove the administration member 110 from the patient's tissue 111 and/or that the tissue back pressure has fallen below the threshold and thus the drug delivery device can be removed from the patient's skin with little or no risk of drug leakage at the injection site.

An opening 136 may be formed in the bottom wall 126, and optionally a sterile barrier or seal member 138, such as a pierceable septum, may extend across the opening 136 to seal the interior of the housing 122 prior to use. In some embodiments, the seal member 138 may be omitted, and instead a removable sealing member (not illustrated) may cover and seal close the opening 136 prior to use.

Figure 3:
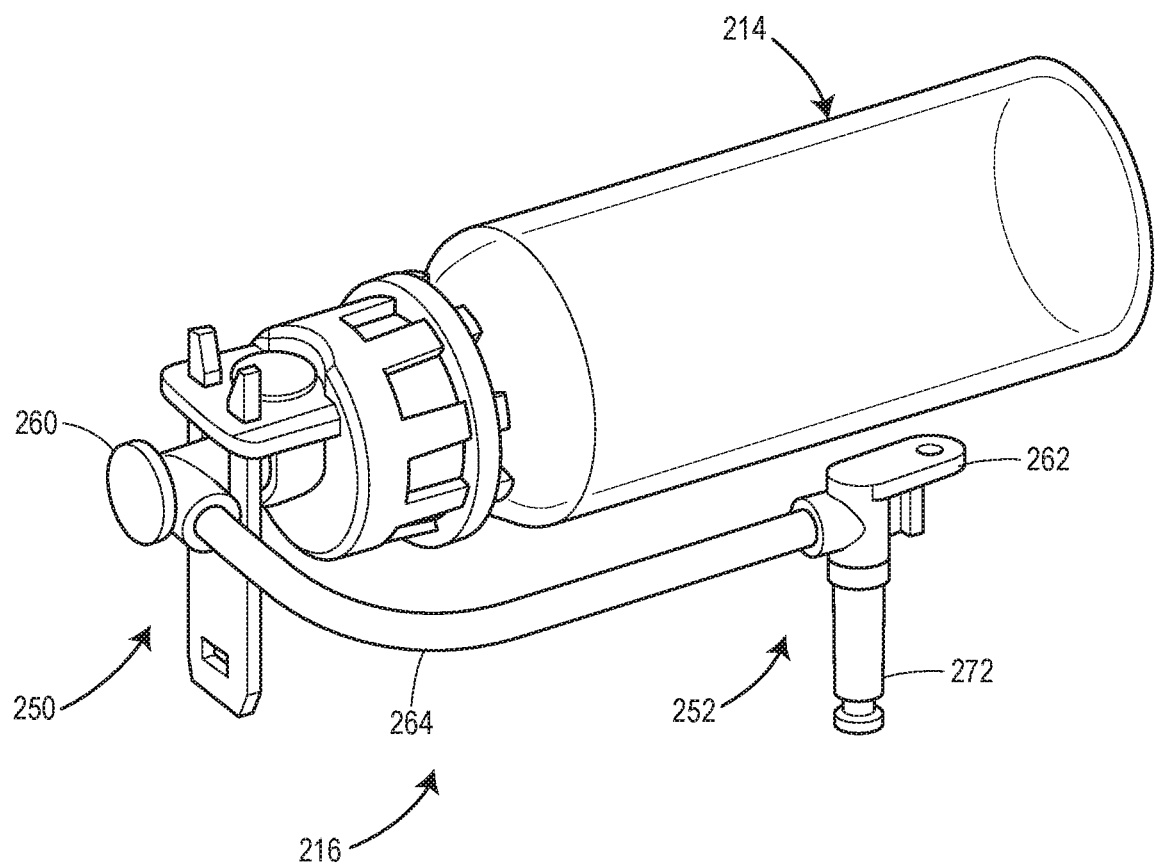
FIG. 3 illustrates a perspective view of a fluid pathway connection assembly according to an embodiment of the present disclosure.

After the bottom wall 126 of the housing 122 is attached to the patient's skin surface 128, the insertion/retraction mechanism 112 may be activated to automatically move the administration member 110, jointly together with the introducer member 113, from a retracted or storage position within the housing 122 to a deployed or operative position extending outside of the housing 122 as seen in FIG. 3. In the present embodiment, this may include the insertion/retraction mechanism 112 inserting the introducer member 113 and the administration member 110 surrounding the introducer member 113 through the seal member 138 and into the patient's tissue 111, as illustrated in FIG. 2. Immediately or shortly thereafter, the insertion/retraction mechanism 112 may automatically retract the introducer member 113, leaving the second end of the administration member 110 inside the patient for subcutaneous delivery of the drug from the reservoir 114. The introducer member 113 may be solid and have a sharpened end to assist with piercing the patient's skin surface 128.

In some embodiments, the insertion/retraction mechanism 112 may include one or more springs (e.g., helical compression springs, helical extension springs, helical torsion springs, spiral torsion springs, etc.) initially retained in an energized state, and which are released upon depression of the activation member 124 in order to insert the administration member 110 and the introducer member 113 into the patient. Furthermore, retraction of the introducer member 113 may be achieved by the automatic release of another spring included in the insertion/retraction mechanism 112 after the administration member 110 and the introducer member 113 have been inserted into the patient. Furthermore, at an appropriate time after drug delivery is complete, retraction of the administration member 110 from the patient's tissue 111 back inside the interior space of the housing 122 may be achieved by the automatic release of another spring included in the insertion/retraction mechanism 112. Other power sources for insertion and/or retraction are possible, including, for example, an electric motor, a hydraulic or pneumatic pump, or a canister that releases a pressurized gas or pressurized liquid to provide actuation energy.

Still referring to FIG. 2, the reservoir 114, which in some contexts may be referred to as a primary container, may include a wall 140 with an interior surface defining an interior space or chamber that is filled or fillable with the drug, and an exterior surface. In some embodiments, the reservoir 114 may be pre-filled with the drug by a drug manufacturer prior to installation of the reservoir 114 in the housing 122. In some embodiments, the reservoir 114 may be rigidly connected to the housing 122 such that the reservoir 114 cannot move relative to the housing; whereas, in other embodiments, the reservoir 114 may be slidably connected to the housing 122 such that the reservoir 114 can move relative to the housing 122 during operation of the drug delivery system 100. The reservoir 114 may have an elongate, barrel-like or cylindrical shape extending along a longitudinal axis A. In some embodiments, the longitudinal axis A of the reservoir 114 may be perpendicular or substantially perpendicular, or otherwise non-parallel, to a direction in which the insertion/retraction mechanism 112 inserts the administration member 110 into the patient. This configuration may allow the on-body injector to have a generally planar, low-profile shape that can be worn by the patient without impeding movement of the patient's limbs. Initially, a stopper 142 or other plunger member may be positioned inside a proximal end 144 of the reservoir 114. The stopper 142 may sealingly and slidably engage the interior surface of the wall 140 of the reservoir 114, and may be movable relative to the wall 140 of the reservoir 114 to expel the drug from the reservoir 114.

The volume of the drug contained in the reservoir 114 may be: any volume in a range between approximately (e.g., ±10%) 0.5-50 mL, or any volume in a range between approximately (e.g., ±10%) 0.5-25 mL, any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., ±10%) 1-3 mL, or any volume in a range between approximately (e.g., ±10%) 1-2.5 mL, or any volume equal to or greater than approximately (e.g., ±10%) 1 mL, or any volume equal to or greater than approximately (e.g., ±10%) 2.5 mL, or any volume equal to or greater than approximately (e.g., ±10%) 10 mL, or any volume equal to or greater than approximately (e.g., ±10%) 25 mL, or any volume equal to or greater than approximately (e.g., ±10%) 50 mL.

During operation of the drug delivery system 100, the drive assembly 118 may push the stopper 142 along the longitudinal axis A from the proximal end 144 to the distal end 145 of the reservoir 114 in order to expel drug from the reservoir 114. In some embodiments, the drive assembly 118 may include one or more springs (e.g., helical compression springs, helical extension springs, helical torsion springs, spiral torsion springs, etc.) initially retained in an energized state, and which are released upon depression of the activation member 124 and/or another actuator. Following their release, the spring(s) may expand or contract to move the stopper 142 through the reservoir 114 to expel the drug. In other embodiments, the drive assembly 118 may include an electric motor which rotates a gear mechanism, including for example one or more sprocket gears, to cause axial motion of the stopper 142 through the reservoir 114. In still further embodiments, the drive assembly 118 may include both an electric motor and spring(s), wherein the electric motor regulates expansion of the spring(s) via a tether or pulley system. In still further embodiments, the drive assembly 118 may include a canister that releases a pressurized gas or pressurized liquid to provide actuation energy.

At the distal end 145 of the reservoir 114, an opening may be formed in a distal end surface of the wall 140. The distal end surface may define a portion of the exterior surface of the wall 140. Prior to use of the drug delivery system 100, the opening may be covered and sealed closed by a sterile barrier or seal member 146, such as a pierceable septum, connected to the distal end 145 of the reservoir 114. Generally, the seal member 146 may be configured to selectively permit access to the drug-containing chamber of the reservoir 114. During operation of the drug delivery system 100, the seal member 146 may be physically altered (e.g., pierced) to permit fluid communication with the drug in the reservoir 114. In some embodiments, the seal member 146 may be constructed of a flexible or elastically deformable material such as rubber, for example, which is capable of being penetrated or pierced by, respectively, a sharpened end or point 148 of a container access needle 149 included as part of the fluid pathway connection assembly 116.

With continued reference to FIG. 2, the fluid pathway connection assembly 116 may be configured to selectively establish fluid communication between the reservoir 114 and the administration member 110 via a sterile fluid flow path during use of the drug delivery system 100. The fluid pathway connection assembly 116 may include a first end 150 connected or connectable in fluid communication with the reservoir 114, a second end 152 connected or connectable in fluid communication with the administration member 110. Prior to use of the drug delivery system 100, the fluid pathway connection assembly 116 may not be in fluid communication with the reservoir 114. During setup of the drug delivery system 100, or during operation of the drug delivery system 100 but prior to drug delivery, the user may manually, or the drug delivery system 100 may automatically, enable, connect, or open the necessary connections to establish fluid communication between the reservoir 114 and the administration member 110 via the fluid pathway connection assembly 116. Subsequently, the drive assembly 118 may move the stopper 142 in the distal direction to force the drug through the sterile fluid flow path of the fluid pathway connection assembly 116 and into the administration member 110 for delivery into the patient's tissue 111.

Still referring to FIG. 2, the first end 150 of the fluid pathway connection assembly 116 may include the container access needle 149. Prior to activation of the fluid pathway connection assembly 116, the container access needle 149 may be retained in a storage position wherein the proximal end of the container access needle 149 is disposed exterior to, and thus not in fluid communication with, the drug-containing chamber of the reservoir 114 (as seen in FIG. 3). After activation of the fluid pathway connection assembly 116, the container access needle 149 may move in a direction toward the reservoir 114 and into an operational position wherein the proximal end of the container access needle 149 is in fluid communication with the reservoir 114. Subsequently, the drive assembly 118 may move the stopper 142 in the distal direction to expel the drug through the container access needle 149, then through a sterile fluid flow path of the fluid pathway connection assembly 116, and then into the administration member 110 for injection into to the patient's tissue 111.

As illustrated in FIG. 2, the drug delivery system 100 may include a pressure sensor 170 mounted adjacent the second end 152 of the fluid pathway connection assembly 116. The pressure sensor 170 may be configured to detect at least tissue back pressure during use of the drug delivery system 100. In some embodiments, the pressure sensor 170 may be configured to detect fluid pressure within an internal fluid flow path of a drug delivery system 100 both (i) during a time period when the drive assembly 118 is operated to deliver a dose of the drug from the reservoir 114 to the patient and (ii) during a time period after delivery of the dose is complete. During operation of the drive assembly 118, the pressure sensor 170 may detect pressure resulting from the force exerted on the drug by the drive assembly 118 and pressure resulting from the force exerted on the drug by the patient's tissue 111, collectively referred to herein as drive pressure. After delivery of the dose of the drug is complete, the pressure (referred to herein as tissue back pressure) detected by the pressure sensor 170 may correspond solely or primarily to that resulting from the force exerted on the drug by the tissue of the patient 116. The tissue back pressure measurement may be possible because the pressure sensor 170 may remain in fluid communication with the interior of the patient's body at the injection site via the administration member 110 after dose completion and prior to removal of the administration member 110 from the patient. During this time period, a volume of residual fluid, including, e.g., bodily fluid, the drug, or a combination of both, may remain within the internal fluid flow path of the drug delivery system 100, or at least within the fluid flow path between the pressure sensor 170 and the outlet of the administration member 110. As a consequence of being exposed to the residual fluid, the pressure sensor 170 is able to make a tissue back pressure measurement.

In addition to or as an alternative to the pressure measurements described in the preceding paragraph, the pressure sensor 170 may be configured to measure pressure within the internal fluid flow path of the drug delivery system 100 during a time period following activation of the insertion/retraction mechanism 112 to insert the administration member 110 into the patient and prior to activation of the drive assembly 118 to expel the drug from the reservoir. Such a measurement may facilitate a determination of whether or not the administration member 110 has been successfully inserted into the patient's tissue 111. When the administration member 110 is initially inserted into the patient, the pressure sensor 170 may detect an increase in pressure due to tissue back pressure. This pressure increase can be interpreted to correspond to successful insertion of the administration member 110 according to some embodiments.

The pressure sensor 170 may be configured to detect pressures in a range between approximately (e.g., ±10%) 0-100 psi, or in a range between approximately (e.g., ±10%) 0-10 psi, or in a range between approximately (e.g., ±10%) 1-10 psi, or in a range between approximately (e.g., ±10%) 1-5 psi. In some embodiments, the maximum pressure detectable by the pressure sensor 170 may be equal to or less than approximately (e.g., ±10%) 100 psi, or equal to or less than approximately (e.g., ±10%) 10 psi, or equal to or less than approximately (e.g., ±10%) 5 psi. Furthermore, in some embodiments the minimum pressure detectable by the pressure sensor 170 may be equal to or less than approximately (e.g., ±10%) 0.5 psi. In some embodiments, the pressure sensor 170 may be optimized for detecting tissue back pressures, which may be relatively low as compared to the drive pressures occurring during operation of the drive assembly 118 to inject the drug.

With continued reference to FIG. 2, in addition to or as an alternative to the pressure sensor 170, the drug delivery system 100 may include a pressure sensor 190 configured to detect drive pressure during use of the drug delivery system 100. This may be accomplished in certain embodiments by configuring the pressure sensor 190 to detect fluid pressure within an internal fluid flow path of the drug delivery system 100 during operation of the drive assembly 118 to expel a dose of the drug from the reservoir 114 to the patient. In some embodiments, the pressure sensor 190 may be mounted adjacent the first end 150 of the fluid pathway connection assembly 116 upstream of the pressure sensor 170 as shown in FIG. 2, although other mounting locations are possible too.

Whereas the pressure sensor 170 may be optimized for detecting relatively low tissue back pressures, the pressure sensor 190 may be optimized for detecting relatively high drive pressures. In some embodiments, the pressure sensor 190 may be configured to detect pressures in a range between approximately (e.g., ±10%) 10-1000 psi, or in a range between approximately (e.g., ±10%) 10-100 psi, or in a range between approximately (e.g., ±10%) 10-50 psi, or greater than or equal to (e.g., ±10%) 10 psi, or greater than or equal to (e.g., ±10%) 20 psi. In some embodiments, the maximum pressure detectable by the pressure sensor 190 may be equal to or greater than approximately (e.g., ±10%) 50 psi, or equal to or greater than approximately (e.g., ±10%) 100 psi. Furthermore, in some embodiments the minimum pressure detectable by the pressure sensor 190 may be equal to or greater than approximately (e.g., ±10%) 10 psi.

Consistent with the intended functions of the pressure sensors 170 and 190, in some embodiments, a minimum pressure detectable by the pressure sensor 170 may be lower than a minimum pressure detectable by the pressure sensor 190; and/or a maximum pressure detectable by the pressure sensor 190 may higher than a maximum pressure detectable by the pressure sensor 170.

While the embodiment illustrated in FIG. 2 utilizes the pressure sensors 170 and 190 for measuring, respectively, tissue back pressure and drive pressure, alternative embodiments may omit the pressure sensor 190 and instead rely on the pressure sensor 170 for measuring both tissue back pressure and drive pressure. Use of a single sensor to measure both tissue back pressure and drive pressure reduces the number of parts and can save costs in certain cases. In such alternative embodiments, the pressure sensor 170 may be able to resolve the relatively low pressures associated with tissue back pressure as well as the relatively high pressures associated with drive pressure. For example, the pressure sensor 170 may be configured to detect pressures in a range between approximately (e.g., ±10%) 0-100 psi; or a minimum pressure detectable by the pressure sensor 170 may be equal to or less than approximately (e.g., ±10%) 0.5 psi and a maximum pressure detectable by the pressure sensor 170 may be equal to or greater than 50 psi.

Referring to FIG. 2, the drug delivery system 100 may include an end-of-dose sensor 192 configured to output a signal indicative of the stopper 142 having reached an end-of-dose position. In the end-of-dose position, the stopper 142 will have expelled an intended dose of the drug from the reservoir 114. In a bolus injector configuration of the drug delivery system 100, for example, the end-of-dose position may correspond to the stopper 142 contacting and stopping at a proximally-facing surface at the distal end 145 of the reservoir 114. In certain such embodiments, the end-of-dose sensor 192 may directly measure the position of the stopper 142 via optical means, electrical means, magnetic means, a physical contact switch, and/or any other suitable sensing technique. In certain such embodiments, the end-of-dose sensor 192 may be mounted on or adjacent to a distal end 145 of the reservoir 114, as illustrated in FIG. 2. In alternative embodiments, the end-of-dose sensor 192 may indirectly measure the position of the stopper 142 by monitoring the movement or position of an element used for driving the stopper 142 such as a motor, spring, plunger rod, tether, etc. In an embodiment where a motor is being monitored, the end-of-dose sensor 192 may measure a rotational position of the motor via optical means, electrical means, magnetic means, a physical contact switch, an encoder, and/or any other suitable sensing technique.

Figure 4:
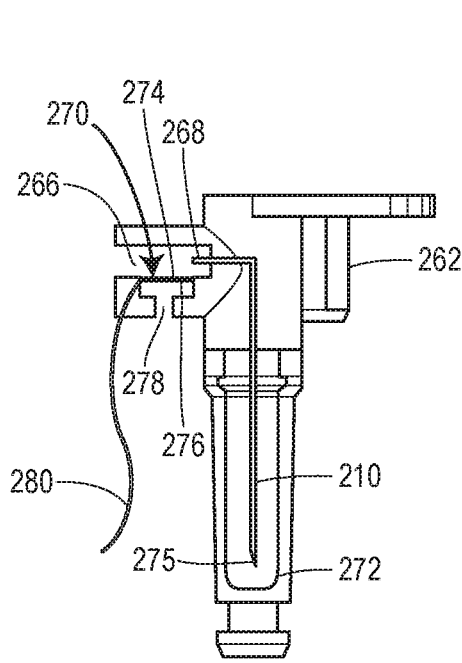
FIG. 4 illustrates a cross-sectional view of a connection hub illustrated in FIG. 3, which has an internally mounted pressure sensor.

Turning to FIGS. 3 and 4, illustrated is an embodiment of the fluid pathway connection assembly described above. The fluid pathway connection assembly and other elements illustrated in FIGS. 3 and 4 may be similar in function and/or structure to the fluid pathway connection assembly 116 and other elements illustrated in FIGS. 1 and 2. Similar elements are assigned with the same reference numerals as in FIGS. 1 and 2, except incremented by 100 in FIGS. 3 and 4. A description of some of these elements is abbreviated or eliminated in the interest of conciseness. The fluid pathway connection assembly 216 may be implemented in the drug delivery system 100 illustrated in FIGS. 1 and 2, for example.

FIG. 3 illustrates that a first or inlet end 250 of the fluid pathway connection assembly 216 is defined by a first connection hub or fitting 260 connected to the reservoir 214, and that a second or outlet end 252 of the fluid pathway connection assembly 216 is defined by a second connection hub or fitting 262 connected to the administration member 210. Extending between and connecting the first connection hub 260 and the second connection hub 262 is a tubular conduit 264. The tubular conduit 264 may, in certain embodiments, be formed entirely or partially by a flexible tube or other hollow elongate structure and may be constructed of a polymeric material such as plastic. In alternative embodiments, a portion of or the entirety of tubular conduit 264 may be made of a rigid material such as metal. Initially there may be slack in the tubular conduit 264 so as to allow the first connection hub 260 and/or the second connection hub 262 to move relative to the reservoir 214 and/or housing (e.g., housing 122) of the drug delivery system. Flexibility in the tubular conduit 264 may facilitate reservoir filling with standard fill-finish equipment and/or installation of the fluid pathway connection assembly 216 within the housing. The tubular conduit 264 may be a single, one-piece structure, or alternatively, formed by multiple interconnected structures.

In some embodiments, the first connection hub 260 may provide a rigid mount for a container access needle (e.g., the container access needle 149 in FIG. 2), and may provide fluid communication between the container access needle and the tubular conduit 264 during use of the drug delivery system, including drug delivery. In some embodiments, the container access needle may be rigidly or fixedly connected to the first connection hub 260 such that the container access needle and the first connection hub 260 are immovable relative to each other and move together as a single unit during, for example, access of the drug-containing chamber of the reservoir 214 by the container access needle during use of the drug delivery system.

Referring to FIG. 4, the second connection hub 262 may provide a rigid mount for the administration member 210, and may provide fluid communication between the tubular conduit 264 and the administration member 210 during use of the drug delivery system, including drug delivery. In some embodiments, the administration member 210 may be rigidly or fixedly connected to the second connection hub 262 such that the administration member 210 and the second connection hub 262 are immovable relative to each other and move together as a single unit during, for example, insertion of the administration member 210 into the patient's tissue and/or retraction of the administration member 210 from the patient's tissue.

According to some embodiments, the second connection hub 262 is rigid, whether according to the nature of the material that defines the second connection hub 262 or according to the nature of the structure of the second connection hub 262. The rigidity of the second connection hub 262 may allow it to hold an end of the tubular conduit 264 and the administration member 210 in a fixed orientation (e.g., a perpendicular or substantially perpendicular orientation) relative to each other during insertion and/or retraction movements. In some embodiments, the connection hub 262 may be constructed of a more rigid (i.e., less flexible) material than that which is used to construct the tubular conduit 264.

As a brief aside, in certain alternative embodiments, the administration member 210 may instead correspond to the introducer member 113 described in connection with FIG. 2. In such alternative embodiments, the administration member 210 would remain in fluid communication with another administration member implanted within the patient's tissue following the retraction of the administration member 210. Accordingly, the drug would pass through the administration member 210 on its way to the implanted administration member.

FIG. 4 illustrates that an internal passageway 266 may be formed within the second connection hub 262. The internal passageway 266 may be configured to provide direct fluid communication between an outlet of the tubular conduit 264 and an inlet 268 of the administration member 210 during use of the drug delivery system, including drug delivery. In some embodiments, the internal passageway 266, or at least a portion thereof, may have a larger inner dimension (e.g., internal diameter) than the inlet 268 of the administration member 210. As described in more detail below, a pressure sensor 270 may be mounted within or on the second connection hub 262 such that the pressure sensor 270 is in fluid communication with the internal passageway 266 of the second connection hub 262 at a location downstream of the outlet of the tubular conduit 264 and upstream of an inlet 268 of the administration member 210.

Another function of the second connection hub 262 is that it may serve as a mount for a shield member 272 that covers an outlet 275 of the administration member 210, as shown in FIG. 4. The shield member 272 may act as a sterile barrier that prevents contamination of the administration member 210 during manufacture and/or storage of the of the drug delivery system. Prior to use of the drug delivery system, the shield member 272 may be detached from the second connection hub 262 to expose the outlet 275 of the administration member 210. In certain embodiments, the shield member 272 may be configured as a rigid needle shield (RNS). In alternative embodiments, the shield member 272 may be omitted.

The second connection hub 262 may be operationally and/or structurally integrated with the mechanism for inserting and/or retracting the administration member 210 such as the insertion/retraction mechanism 112 described above in connection with FIG. 2. Operation of the insertion/retraction mechanism may cause the second connection hub 262 and any components mounted thereto to move relative to the patient and/or other elements of the drug delivery system such as the housing 122. For example, during insertion of the administration member 210 into the patient, the insertion/retraction mechanism may cause the second connection hub 262, the pressure sensor 270, and the administration member 210 to move jointly together toward the patient and relative to the housing 122. During retraction of the administration member 210 from the patient, the insertion/retraction mechanism may cause the second connection hub 262, the pressure sensor 270, and the administration member 210 to move jointly together away from the patient and relative to the housing 122.

In the embodiment illustrated in FIG. 4, the pressure sensor 270 is disposed in-line with the fluid flow path provided by the fluid pathway connection assembly 216 during use of the drug delivery system. More particularly, the pressure sensor 270 is mounted within the second connection hub 262 and arranged to have a first surface 274 exposed to fluid pressure within the internal passageway 266. A second surface 276 of the pressure sensor 270 is exposed to ambient pressure (e.g., atmospheric pressure) or ambient air by way of a side port 278 formed in a wall of the second connection hub 262. So configured, the pressure sensor 270 may be able to measure the pressure within the internal passageway 266 relative to ambient pressure. In some embodiments, the drug may come into direct contact with the first surface 274 of the pressure sensor 270 during use of the drug delivery system, though that is not required.

In some embodiments, the first surface 274 and the second surface 276 of the pressure sensor 270 may be defined by opposite sides of a flexible diaphragm or membrane. The diaphragm may undergo elastic deformation or deflection when the pressure within the internal passageway 266 differs from ambient pressure. That elastic deformation can be interpreted to correspond to fluid pressure within the internal passageway 266. This may involve the diaphragm interfacing with a resistive, capacitive, or other electrical element. A capacitive-type pressure sensor may involve the use of a thin diaphragm as one plate of a capacitor. Applied pressure may cause the diaphragm to deflect and the capacitance to change. The change in capacitance may be proportional to the applied pressure.

In a semiconductor-based configuration, the pressure sensor 270 may include a piezo-resistive pressure measuring cell including a thin silicon membrane. Disposed on the silicon membrane may be one or more, or four, resistors in the form of impurity atoms implanted in the silicon crystal lattice. When a pressure is applied to the silicon membrane, resistances change because of mechanical stress on the silicon membrane. This is commonly referred to as the piezo-resistive effect. The resistors may be connected in a Wheatstone bridge such that when supplied with an electrical potential, an electric output signal is generated that is proportional to the applied pressure. Other configurations of the pressure sensor 270 are also possible.

The pressure sensor 270 may output a signal representative of the pressure measurement to a controller (e.g., the controller 120) of the drug delivery system via a wired or wireless connection. In FIG. 4, an electrical lead or wire 280 communicatively couples the pressure sensor 270 with the controller.

As illustrated in FIG. 4, the pressure sensor 270 may be arranged immediately upstream of the inlet 268 of the administration member 210 and downstream of the outlet of the tubular conduit 264. A direct or non-tortuous fluid flow path may exist between the pressure sensor 270 and the inlet 268 of the administration member 210 by virtue of the pressure sensor 270 being arranged immediately upstream of the inlet 268 of the administration member 210. In some embodiments, the distance between the first surface 274 of the pressure sensor 270 and the inlet 268 of the administration member 210 may be equal to or less than approximately (e.g., ±10%) 10 mm, or equal to or less than approximately (e.g., ±10%) 5 mm. Positioning the pressure sensor 270 immediately upstream of the inlet 268 of the administration member 210 may allow the pressure sensor 270 to make more accurate measurements of tissue back pressure.

In some embodiments, the pressure sensor 270 may be integrated or embedded, entirely or partially, within the wall of the second connection hub 262, as illustrated in FIG. 4. Here, the pressure sensor 270 may share an external injection molding housing with the second connection hub 262. Such a configuration may simplify or streamline assembly of the pressure sensor 270 with the drug delivery system. In other embodiments, the pressure sensor 270 may be separate from the second connection hub 262. In such embodiments, the pressure sensor 270 may be connected to the second connection hub 262 via a fastener such as a screw.

The pressure sensor 270 may be used to detect fluid pressure of the drug in the internal passageway 266 of the second connection hub 262 both (i) during a time period when a drive assembly is operated to deliver a dose of the drug from a reservoir to the patient and (ii) during a time period after delivery of the dose is complete. During operation of the drive assembly, the pressure sensor 270 may detect a combination of drive pressure and tissue back pressure. After drug delivery is complete, the pressure detected by the pressure sensor 270 may correspond solely or primarily to tissue back pressure. The tissue back pressure measurement may be possible because the pressure sensor 170 may remain in fluid communication with the interior of the patient's body at the injection site via the administration member 110 after dose completion and prior to removal of the administration member 110 from the patient. During this time period, a volume of residual fluid, including, e.g., bodily fluid, the drug, or a combination of both, may remain within the internal passageway 266 of the second connection hub 262 and the administration member 110. As a consequence, the pressure sensor 170 is exposed to the residual fluid and thus able to make a tissue back pressure measurement.

In addition to or as an alternative to the pressure measurements described in the preceding paragraph, the pressure sensor 270 may be used to measure pressure within the internal passageway 266 during a time period following activation of an insertion/retraction mechanism to insert an administration member into the patient and prior to activation of the drive assembly to expel the drug from the reservoir. Such a measurement may facilitate a determination of whether or not the administration member has been successfully inserted into the patient's tissue. When the administration member is inserted into the patient, the pressure sensor 270 may detect an increase in pressure due to tissue back pressure. This increase can be interpreted to correspond to successful insertion of the administration member.

In addition to the pressure sensor 270, in some embodiments the second connection hub 262 may incorporate a pressure sensor configured to detect drive pressure. This additional pressure sensor may include characteristics similar to the pressure sensor 190 described above in connection with FIG. 2. Furthermore, this additional pressure may be located upstream or pressure sensor 270 in some embodiments.

Figure 5:
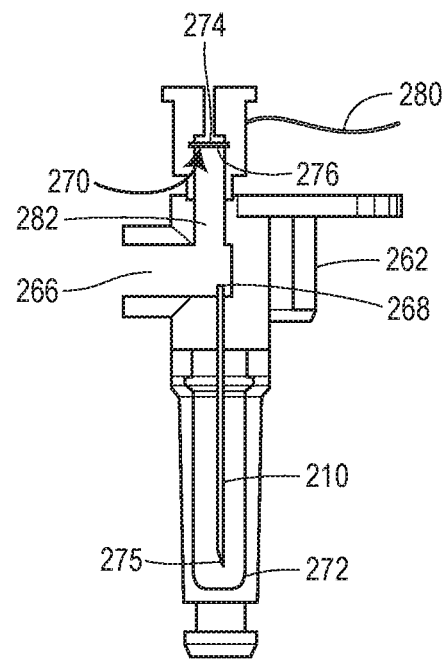
FIG. 5 illustrates a cross-sectional view of a connection hub according to an embodiment of the present disclosure, with an externally mounted pressure sensor.

Referring to FIG. 5, illustrated is an alternative embodiment of a pressure sensor 270 where it is mounted on the outside of the second connection hub 262. Here, the second connection hub 262 has a side port 282 that extends between an exterior surface of the second connection hub 262 and the internal passageway 266. The pressure sensor 270 may be in fluid communication with the internal passageway 266 via the side port 282. Similar to the FIG. 4 embodiment, the first surface 274 of pressure sensor 270 may be exposed to the drug and the second surface 276 of the pressure sensor 270 may be exposed to ambient air. Mounting the pressure sensor 270 on the outside of the second connection hub 262 may facilitate designs where the pressure sensor 270 is manufactured separately from the second connection hub 262 or is an add-on component to be combined with an existing connection hub design.

While the foregoing embodiments of the pressure sensor are mounted within or on the second connection hub, alternative embodiments may involve mounting the pressure sensor elsewhere within the drug delivery system. For example, the pressure sensor may be mounted within or on the administration member, the tubular conduit, the first connection hub, or the reservoir.

Figure 6:
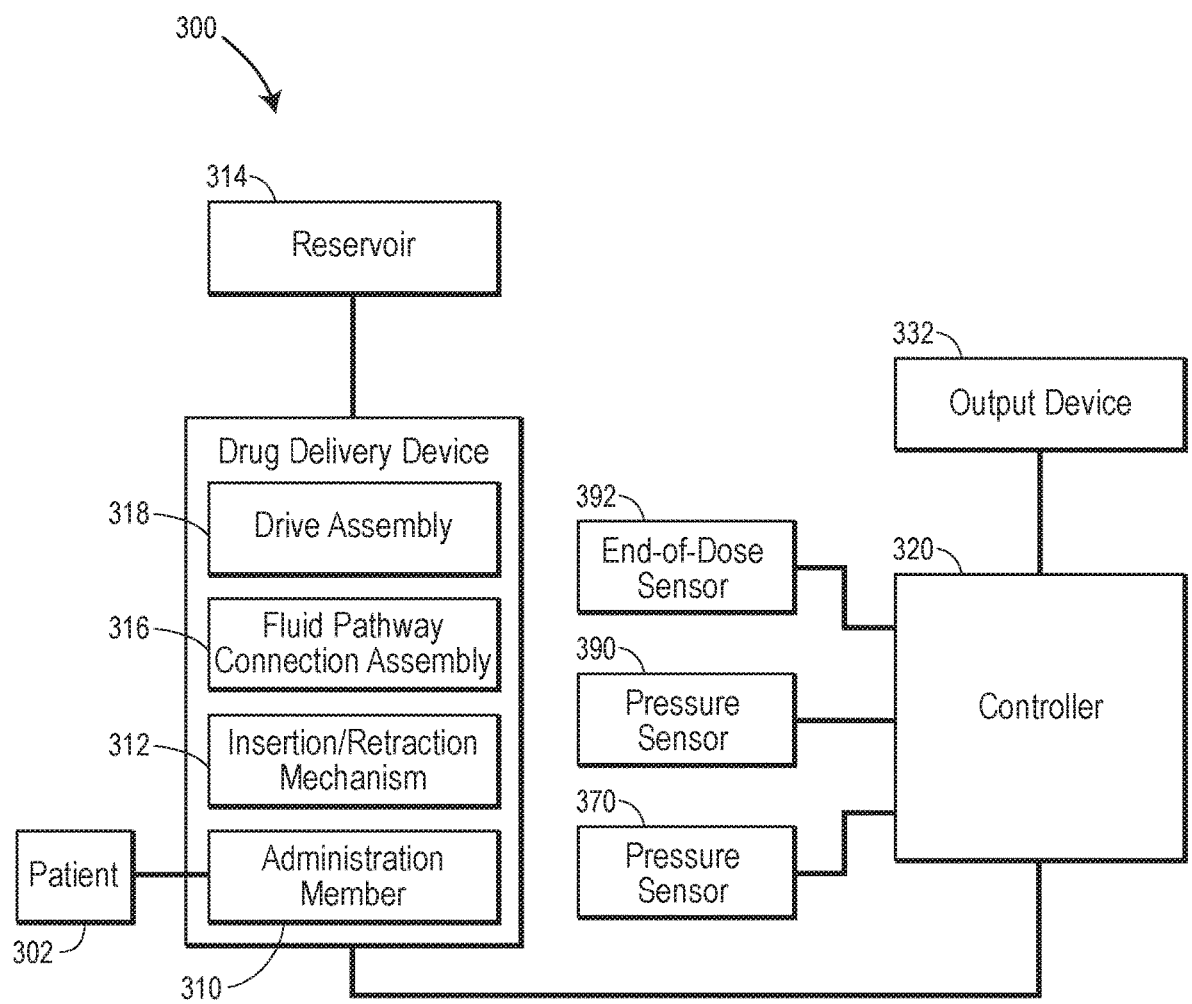
FIG. 6 illustrates a schematic view of a drug delivery system according to one embodiment of the disclosure.

FIG. 6 is a block diagram schematically illustrating an embodiment of a drug delivery system 300 according to the present disclosure. The drug delivery system 300 may be associated with a patient 302, who may use the drug delivery system 300 to inject or infuse a drug into tissue as part of a therapeutic regimen. Various elements of the drug delivery system 300 may be similar in function and/or structure to those of the drug delivery system 100 described in connection with FIGS. 1 and 2. Similar elements are assigned with the same reference numerals as in FIGS. 1 and 2, except incremented by 200 in FIG. 6. A description of some of these elements is abbreviated or eliminated in the interest of conciseness. Furthermore, the drug delivery system 300 may integrate the components described in connection FIGS. 3-5, where appropriate.

Similar to the drug delivery system 100, the drug delivery system 300 includes an administration member 110, an insertion/retraction mechanism 112 for automatically inserting and/or retracting the administration member 110 into/from a patient 302, a reservoir 314 connected or connectable in fluid communication with the administration member 110 via a fluid pathway connection assembly 316, a drive assembly 318 configured to actuate the reservoir 314 to deliver the drug to the patient 302 via the administration member 310, a controller 320, an output device 332 controllable to notify and/or provide information to the patient or user about the operational state or condition of the drug delivery system 300, a pressure sensor 370 configured to detect tissue back pressure during use of the drug delivery system 300, a pressure sensor 390 configured to detect drive pressure during use of the drug delivery system 300, and an end-of-dose sensor 392. The drug delivery system 300 may also include other elements and/or functionalities of the drug delivery system 100, in certain embodiments. In certain alternative embodiments, the pressure sensor 390 may be omitted, and both tissue back pressure and drive pressure measurements may be made via the pressure sensor 370.

The controller 320 may be configured to control the operation of various component(s) of the drug delivery system 300, including, for example, the insertion/retraction mechanism 312, the drive assembly 318, and the output device 332. Further, the controller 320 may be configured to receive and/or process information, data, signals (analog and/or digital), or other output from the pressure sensor 370, the pressure sensor 390, the end-of-dose sensor 392, and/or other elements of the drug delivery system 300 and/or external elements such as a smartphone. Furthermore, the controller 320 may be responsive to the output it receives from such element(s), and may be configured to automatically control the operation of certain element(s) such as the insertion/retraction mechanism 312, the drive assembly 318, and/or the output device 332 according to the programming or other configuration of the controller 320.

The controller 320 may include and/or implement its operations via an electrical device (e.g., a hardwired circuit, a microprocessor, etc.), a combination of electrical devices, a mechanical device, a combination of mechanical devices, a chemical device, a combination of chemical devices, or any combination thereof (e.g., an electromechanical device, an electrochemical device, etc.). According to those embodiments wherein the controller 320 includes a microprocessor or the like, the configuration of the controller 320 may correspond to the software or other programming of the controller 320. In some embodiments, the controller 320 may be pre-configured by a manufacturer and/or healthcare provider such that it cannot later be reconfigured by the patient or other end user; whereas, in other embodiments, the controller 320 may be configurable by any individual or entity, within reason.

In some embodiments, the controller 320 may be provided as a computing device that includes one or more processors and one or more memories in communication with or integrated with each other. The one or more processors may include, for example, one or more of a microprocessor, micro-controller, programmable logic controller, digital signal processor, microcomputer, central processing unit, field programmable gate array, logic circuitry, analog circuitry, digital circuitry, software-based processing module, and any device that manipulates signals (analog and/or digital) based on hard coding of the circuitry and/or operational instructions, or any combination thereof. The one or more memories may include a non-transitory computer-readable storage medium configured to store data, including, for example, non-transitory computer-readable instructions constituting one or more services, programs, and/or modules and any data operated on or produced by such services, programs, and/or modules. The memory may store the data on a volatile (e.g., random access memory (RAM), etc.) and/or non-volatile memory (e.g., a hard disk), and may be a removable or non-removable memory. The one or more processors may be configured to fetch and execute the instructions stored in the one or more memories in order to perform or implement various functions of the drug delivery system 300, including, for example, controlling the drive assembly 318 to deliver the drug to the patient 302 according to a dosing regimen, controlling the insertion/retraction mechanism 312 to insert the administration member 310 into the patient and/or retract the administration member 310 from the patient, and/or controlling the output device 332.

In some embodiments, the controller 320 may be coupled (e.g., via wired or wireless connections) with one or more of the insertion/retraction mechanism 312, the drive assembly 318, the output device 332, the pressure sensor 370, the pressure sensor 390, and the end-of-dose sensor 392 such that the controller 320 can transmit communications to and/or receive communications from one or more of the insertion/retraction mechanism 312, the drive assembly 318, the output device 332, the pressure sensor 370, the pressure sensor 390, and the end-of-dose sensor 392. Such communications may be electrical and/or mechanical in nature, and/or may include information, data, and/or signals (analog and/or digital).

According to some embodiments, the controller 320 may be configured to analyze the output (e.g., signals, data, information, etc.) received from the pressure sensor 370, the pressure sensor 390, and/or the end-of-dose sensor 392 and make determinations about the operational state or condition of the drug delivery system 300 and/or the patient 302. Based on those determinations, the controller 320 may control or operate various elements of the drug delivery system 300 in accordance with a routine, program, regimen, etc. for which the controller 320 has been configured. In one such regimen, the controller 320 may be configured to determine if delivery of a dose of a drug to a patient is complete based on the output from the end-of-dose sensor 392. If the controller 320 determines that delivery of the dose of the drug is complete, the controller 320 may be configured to measure tissue back pressure based on output from the pressure sensor 370 and compare it to a predetermined value (e.g., $P_b$ in FIG. 7). If the controller 320 determines that the tissue back pressure is below the predetermined value, then the controller 320 may control (e.g., activate or de-activate) the output device 332 at least once. In some embodiments, this may involve the controller 320 controlling the output device 332 to, for example, display a textual instruction and/or emit a blinking or continuous light informing the patient or user that the administration member 310 can be removed from the patient's tissue. Conversely, if the controller 320 determines that the tissue back pressure is above the predetermined value, then the controller may control (e.g., activate or de-activate) the output device 332 to alert the patient 302 or user that the administration member 310 should not be removed from the patient's tissue because of a concern about drug leakage at the injection site. As an addition to or as an alternative to operating the output device 332 in the event that tissue back pressure is below the predetermined value, the controller 320 may be configured to activate or otherwise control the insertion/retraction mechanism 312 to retract the administration member 310 from the patient 302 should the controller 320 determine that tissue back pressure is below the predetermined value. As a consequence, the administration member 310 may be left within the patient's body and thus able to inhibit drug leakage at the injection site until a time when the injected dose has been sufficiently absorbed by the patient's tissue.

In addition to monitoring tissue back pressure, the controller 320 may be configured to monitor drive pressure based on output from the pressure sensor 390, or if the pressure sensor 390 is omitted, based on output from the pressure sensor 370. In some such embodiments, the controller 320 may be configured to determine if the drive pressure is within a predetermined range, and if not, cease operation of the drive assembly 318 and/or operate the output device 332 to indicate error.

While the foregoing embodiments of the drug delivery system have been described primarily in the context of an on-body injector that is adhered or otherwise attached to the patient's skin over the course of drug delivery, the scope of the present disclose is not limited to such wearable devices. In alternative embodiments, the drug delivery system may be configured as autoinjector or manually-powered syringe that is held in the patient's or users hand over the course of drug delivery. In such alternative embodiments, the drug delivery system may have an elongate shape where a longitudinal axis of the drug reservoir is parallel to a longitudinal axis of the administration member.

Figure 7:
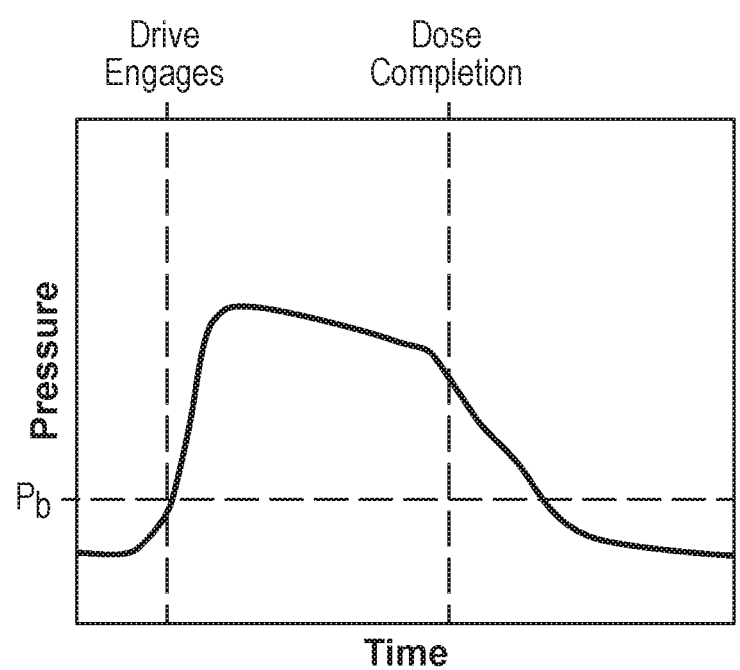
FIG. 7 is a graph illustrating how pressure varies over time during use of a drug delivery system in accordance with principles of the present disclosure.

FIG. 7 illustrates an example of how pressure may vary over the duration of use of any one of the drug delivery systems described above. The pressure may be measured at a location within and/or along an internal fluid flow path of the drug delivery system such as within a fluid pathway connection assembly. Initially, pressure may be equal to or substantially equal to ambient pressure. The pressure rises significantly when the drive assembly of the drug delivery system is engaged to expel a dose of the drug from the reservoir. Upon dose completion (e.g., when a stopper reaches its end-of-dose position), the pressure begins to fall but may not immediately return to ambient pressure due to the presence of tissue back pressure. Tissue back pressure gradually decays as the injected dose of the drug is absorbed or otherwise accommodated within the patient's tissue. When the pressure falls below $P_b$, it may be safe to remove the administration member from the patient's tissue with little or no risk of tissue back pressure causing backflow or leakage of the drug at the injection site.

As will be recognized, the systems, devices, and methods according to the present disclosure may have one or more advantages relative to conventional technology, any one or more of which may be present in a particular embodiment in accordance with the features of the present disclosure included in that embodiment. Other advantages not specifically listed herein may also be recognized as well.

Drug Information above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 146B7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); Vectibix® (panitumumab), Xgeva® (denosumab), Prolia® (denosumab), Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153, 507); Tysabri® (natalizumab, anti-α4integrin mAb); Valortim® (MDX-1303, anti-*B. anthracis* protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-a581 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, or BPS 804 (Novartis) and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoVEXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:
1. A drug delivery system comprising:
a housing;
a reservoir disposed at least partially within the housing and filled or fillable with a drug;
an administration member connected or connectable in fluid communication with the reservoir, the administration member having a storage state wherein at least a portion of the administration member is disposed within the housing and operative state wherein the at least a portion of the administration member extends through an opening in the housing for insertion into a patient;

a drive assembly configured to urge the drug from the reservoir and to the patient via the administration member;

a pressure sensor configured to detect at least tissue back pressure during use of the drug delivery system; and wherein the drug delivery system is configured and/or programmed to monitor the tissue back pressure after and/or in response to the drug delivery system having completed delivery of a dose of the drug to the patient.

2. The drug delivery system of claim 1, the pressure sensor being in fluid communication with the administration member following drug delivery and prior to retraction of the administration member from the patient.

3. The drug delivery system of claim 1, the pressure sensor being configured to detect drive pressure during operation of the drive assembly to urge the drug from the reservoir and to the patient.

4. The drug delivery system of claim 1, wherein the pressure sensor is disposed immediately upstream of an inlet of the administration member.

5. The drug delivery system of claim 4, wherein a distance between the pressure sensor and the inlet of the administration member is less than or equal to 10 mm.

6. The drug delivery system of claim 1, wherein at least one of (a) or (b):
(a) a minimum pressure detectable by the pressure sensor is equal to or less than 0.5 psi, or
(b) a maximum pressure detectable by the pressure sensor is less than or equal to 100 psi.

7. The drug delivery system of claim 1, comprising:
a tubular conduit connected or connectable in fluid communication with the reservoir;
a connection hub having an internal passageway configured to provide fluid communication between the tubular conduit and the administration member during use of the drug delivery system; and
the connection hub and the pressure sensor each being disposed downstream of the tubular conduit.

8. The drug delivery system of claim 7, at least a portion of the pressure sensor being mounted within the connection hub.

9. The drug delivery system of claim 8, the pressure sensor including a flexible diaphragm having a first surface and a second surface, wherein, during use of the drug delivery system, the first surface is exposed to fluid pressure within the internal passageway of the connection hub and the second surface is exposed to ambient pressure.

10. The drug delivery system of claim 7, the pressure sensor being mounted outside of the connection hub and configured to be in fluid communication with the internal passageway of the connection hub via a side port formed in the connection hub.

11. The drug delivery system of claim 1, comprising a second pressure sensor configured to detect drive pressure during operation of the drive assembly to urge the drug from the reservoir and to the patient.

12. The drug delivery system of claim 11, wherein at least one of (a) or (b):
(a) a minimum pressure detectable by the pressure sensor is lower than a minimum pressure detectable by the second pressure sensor, or
(b) a maximum pressure detectable by the second pressure sensor is higher than a maximum pressure detectable by the pressure sensor.

13. The drug delivery system of claim 11, wherein the pressure sensor is configured to detect pressures within a first range between 0 and 100 psi or any sub-range within the first range, and the second pressure sensor is configured to detect pressures within a second range between 10 and at least 100 psi or any sub-range within the second range.

14. The drug delivery system of claim 1, comprising a controller coupled to the pressure sensor and configured:
(a) to determine if delivery of the dose of the drug is complete, and if delivery of the dose of the drug is complete, to measure the tissue back pressure; and
(b) to determine if the tissue back pressure is below a predetermined value subsequent to (a).

15. The drug delivery system of claim 14, comprising an output device, wherein the controller is configured to control the output device at least once to notify or alert the patient or a user if the tissue back pressure is below the predetermined value.

16. The drug delivery system of claim 1, comprising an adhesive for removably coupling the housing to skin of the patient.

17. The drug delivery system of claim 16, wherein the housing comprises a wall, the opening is formed in the wall, and the adhesive is configured to removably couple the wall to the skin of the patient.

18. The drug delivery system of claim 17, wherein the pressure sensor is at least partially disposed within the housing.

19. The drug delivery system of claim 1, wherein the pressure sensor is configured to detect tissue back pressure after the drive assembly has completed delivering a dose of the drug to the patient via the administration member.

20. The drug delivery system of claim 1, comprising a controllable element, wherein the drug delivery system is configured and/or programmed to control the controllable element to convey an operational state and/or condition of the drug delivery system to the patient based on at least a tissue back pressure measurement measured after the drug delivery system has completed delivery of the dose of the drug to the patient.

21. A method of operating a drug delivery system, the method comprising:
providing a drug delivery system comprising:
a housing;
a reservoir disposed at least partially within the housing and filled or fillable with a drug;
an administration member connected or connectable in fluid communication with the reservoir, the administration member having a storage state wherein at least a portion of the administration member is disposed within the housing and operative state wherein the at least a portion of the administration member extends through an opening in the housing for insertion into a patient;
a drive assembly configured to urge the drug from the reservoir and to the patient via the administration member;
a pressure sensor configured to detect at least tissue back pressure during use of the drug delivery system; and
wherein the drug delivery system is configured and/or programmed to monitor the tissue back pressure after and/or in response to the drug delivery system having completed delivery of a dose of the drug to the patient;
automatically inserting an end of the administration member initially stored within an interior space of the housing of the drug delivery system into the patient;

automatically actuating the reservoir to deliver the dose of the drug to the patient via the administration member; and using the pressure sensor included in the drug delivery system to monitor tissue back pressure after finishing actuating the reservoir to deliver the dose of the drug to the patient.

\* \* \* \* \*